United States Patent
Casas

(10) Patent No.: US 10,278,480 B2
(45) Date of Patent: May 7, 2019

(54) AURICLE RETAINER

(71) Applicant: Mario Casas, Chicago, IL (US)

(72) Inventor: Mario Casas, Chicago, IL (US)

( * ) Notice: Subject to any disclaimer, the term of this patent is extended or adjusted under 35 U.S.C. 154(b) by 0 days.

(21) Appl. No.: 15/492,115

(22) Filed: Apr. 20, 2017

(65) Prior Publication Data

US 2018/0303223 A1 Oct. 25, 2018

(51) Int. Cl.
*A45D 44/22* (2006.01)
*G02C 11/00* (2006.01)
*G02C 5/14* (2006.01)
*A61F 11/00* (2006.01)

(52) U.S. Cl.
CPC .............. *A45D 44/22* (2013.01); *A61F 11/00* (2013.01); *G02C 5/143* (2013.01); *G02C 11/00* (2013.01)

(58) Field of Classification Search
CPC .................... A45D 44/22; A61F 11/008; A61F 11/00–11/14; G02C 5/143; G02C 11/00–11/12; H04R 25/00–25/75
See application file for complete search history.

(56) References Cited

U.S. PATENT DOCUMENTS

| | | |
|---|---|---|
| 1,050,744 A | 1/1913 | Monier-Williams |
| 1,472,014 A | 11/1922 | Clulee |
| 1,533,190 A | 9/1923 | Jirasek |
| 1,636,740 A | 2/1926 | Hickey |
| 2,229,568 A | 1/1941 | Hodgkins |
| 3,010,365 A | 11/1961 | Sadel |
| 3,741,635 A * | 6/1973 | Wortman ............... G02C 3/003 351/123 |
| 3,958,430 A * | 5/1976 | Barron ................... A44C 7/009 63/14.2 |
| 4,169,665 A * | 10/1979 | McCulloch ............ G02C 3/003 351/111 |
| 4,187,838 A * | 2/1980 | Dubrowski .............. A61F 5/01 606/204.15 |
| D264,476 S | 5/1982 | Stensager |
| 5,076,262 A | 12/1991 | Coffey |
| 6,517,557 B1 * | 2/2003 | Sorribes .................... A61F 5/01 606/1 |
| 7,093,600 B2 | 8/2006 | Sorribes |
| 7,559,647 B2 * | 7/2009 | Curiel .................... G02C 3/003 351/103 |
| 8,715,347 B2 * | 5/2014 | Servell ................. A61B 5/1079 606/204.15 |
| 8,820,921 B1 * | 9/2014 | Lier ........................ G02C 5/143 351/120 |
| 2006/0077340 A1 * | 4/2006 | Curiel .................... G02C 3/003 351/123 |

(Continued)

OTHER PUBLICATIONS

Fendi. Orchidea. Aug. 31, 2015. <http://www.fendi.com:80/us/orchidea-cat-eye-sunglasses/p-FOG251V1WF0323>.*

(Continued)

*Primary Examiner* — Ryan J. Severson
*Assistant Examiner* — Charles M Wei
(74) *Attorney, Agent, or Firm* — Robert M. Schwartz; Alfred K. Dassler

(57) ABSTRACT

Disclosed is an auricle retainer that is configured to conveniently retain an auricle of a wearer. The auricle retainer may include an earpiece and an arm connected to the earpiece. The arm may be configured to engage a helix of the auricle for retaining the auricle.

3 Claims, 7 Drawing Sheets

(56) References Cited

U.S. PATENT DOCUMENTS

| | | | |
|---|---|---|---|
| 2006/0098160 A1* | 5/2006 | Jamie | G02C 3/003 351/123 |
| 2016/0045372 A1* | 2/2016 | Case | A61F 11/004 602/12 |
| 2016/0081562 A1 | 3/2016 | Lachhman | |

OTHER PUBLICATIONS newborns.stanford.edu/PhotoGallery/LopEar1.him.
https://www.google.com/search?q=splint+for+lop+ear&safe=off&biw=1366&bih=601&source=lnms&tbm=isch&sa=X&ved=0ahUKEwiEtpPF4JvMAhXGWz4KHWSIBkkQ_AUIBygC.

\* cited by examiner

AURICLE RETAINER

FIELD OF THE INVENTION

The present invention relates generally to body part support devices and more particularly to a wearable auricle retainer for retaining an auricle of an ear.

BACKGROUND OF THE INVENTION

A human body may not be completely symmetrical. Sometimes, external portions (also known as auricles) of an individual's ears may be nonsymmetrical with respect to one another. For example, one ear may be wider than an opposite ear when an individual's head is frontally viewed.

Such individuals may desire to maintain a symmetrical appearance of their ears.

One solution to this problem would be to apply cosmetic surgery to the individual to correct variances in the individual's ears. However, surgery is invasive, expensive, permanent, painful, and time consuming.

As such, there exists a need for a device for temporarily maintaining a symmetrical appearance of, or pulling back, an individual's ears.

BRIEF SUMMARY OF THE INVENTION

Disclosed is an ear retainer, the retainer comprising, an arm attachable to an earpiece for engaging an ear of a wearer to retain the ear.

In another aspect, the earpiece is a temple tip portion of an eyewear article.

In another aspect, the earpiece is configured to curve around the ear to be supported on the ear.

In another aspect, the arm is malleable.

In another aspect, the arm is covered by a flexible sheath.

In another aspect, the earpiece includes a curve, the curve defining a space for receiving the ear and supporting the earpiece on the ear.

In another aspect, the arm is configured to retain an auricle of the ear toward a head of the wearer.

DETAILED DESCRIPTION OF THE INVENTION

Disclosed is an auricle retainer that is configured to retain, hold and/or support an auricle of an ear. A wearer may have nonsymmetrical ears and may wear the auricle retainer such that the auricles of their ears appear symmetrical. For example, from a front view of the wearer's face, one of the wearer's ears may be larger, or may extend farther away from their head than an opposite ear, and the disclosed auricle retainer may be worn to retain, or pull, an auricle of the larger ear closer to the head of the wearer, allowing the ears to appear symmetrical from a front view of the wearer's face. As such, the auricle retainer when worn may apply a retaining or pulling force on the auricle (e.g. on a superior portion of the helix) toward the wearer's head to retain such a larger ear to a symmetrical or retained position.

It is to be understood that the term "ear" as disclosed herein may invariably refer to an auricle of the ear. The term "head" may refer to portions of a human (wearer) head such as temporal regions of the head which do not include the auricle of the ear. Posterior or back portions or surfaces of the auricle may refer to surfaces of the auricle that normally face toward the head. Further, it is to be understood that the term "earpiece" may invariably refer to an earpiece configured to rest on a user's ear, or an earpiece of eyewear or headwear. For example, an appropriate earpiece may be a temple tip portion of a set of eyeglasses or eyewear or a curved earpiece that individually is configured to rest or hang on a wearer's ear.

Figure 11:
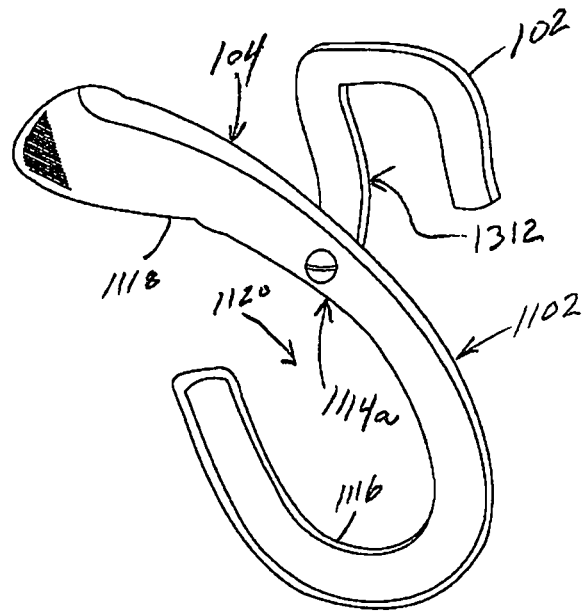
FIG. 11 shows a side view of the auricle retainer of FIG. 5, the auricle retainer attached to an earpiece.
Figure 12:
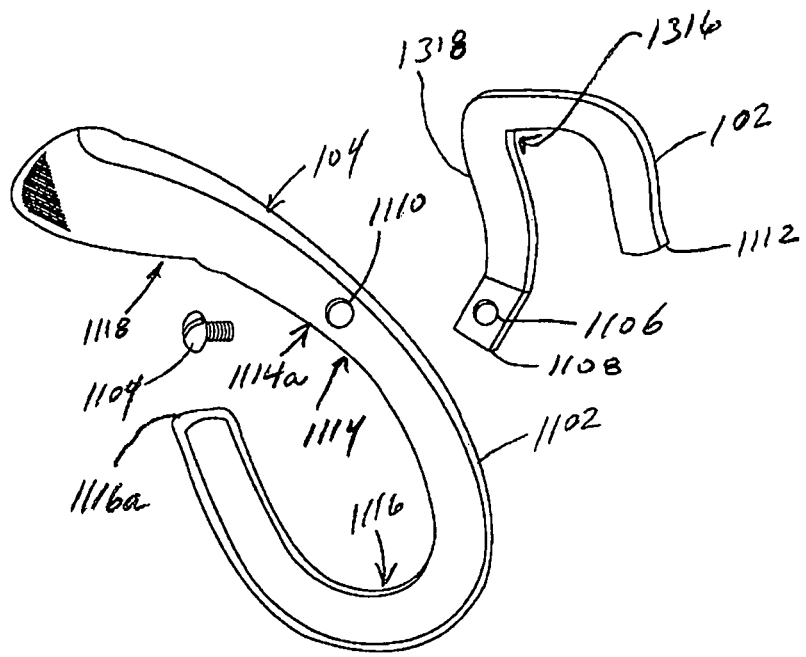
FIG. 12 shows a side view of the auricle retainer of FIG. 11, the auricle retainer detached from the earpiece.
Figure 13:
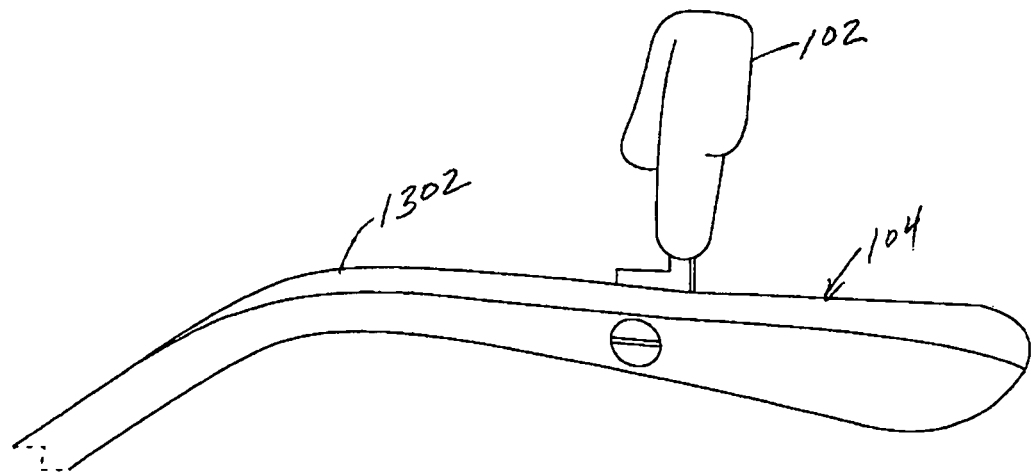
FIG. 13 shows a side view of the auricle retainer of FIG. 1, the auricle retainer attached to eyewear.
Figure 14:
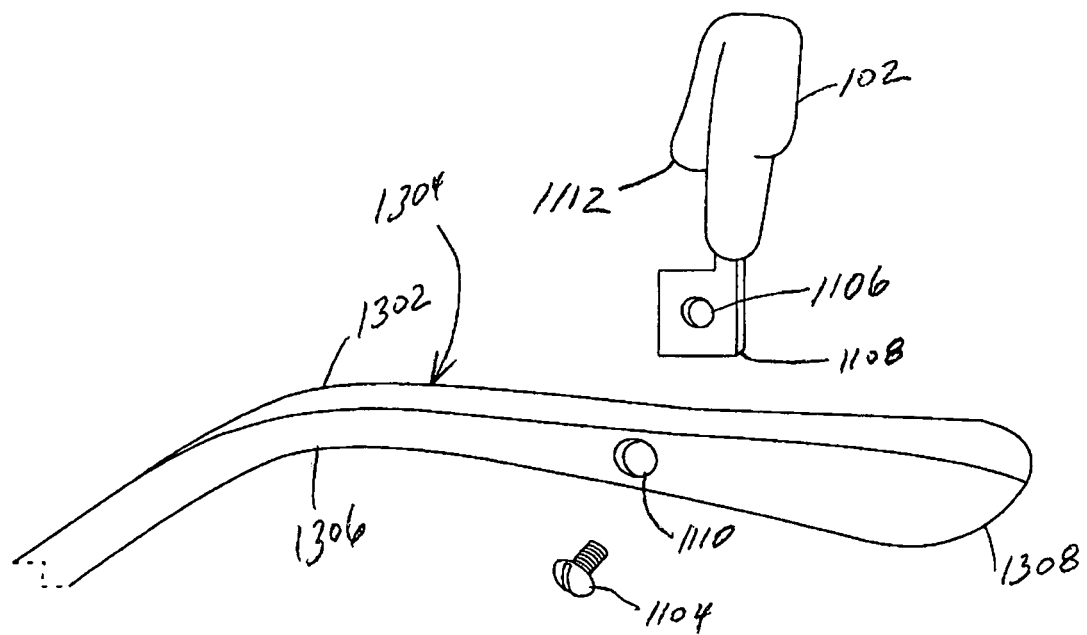
FIG. 14 shows a side view of the auricle retainer of FIG. 1, the auricle retainer detached from the eyewear.

The illustrations of FIGS. 1-14 show examples of an auricle retainer 100 including a hook or arm 102 that is attachable to an earpiece 104 for engaging the arm 102 with an auricle 106 (FIGS. 1-10) of a wearer 108 to retain the auricle 106 when the earpiece 104 is worn. For example, FIGS. 11 and 12 show arm 102 being attachable or attached to a curved earpiece 1102, and FIGS. 13 and 14 show the arm 102 being attachable or attached to an eyewear earpiece 1302. As such, examples of the earpiece 104 may include curved earpiece 1102 or eyewear earpiece 1302. It is to be understood that earpiece 104 may be any appropriate structure that is configured to rest on or near a wearer's auricle.

As shown in FIGS. 11-14, arm 102 may be attached to an earpiece 104 via a screw 1104 (i.e. a bolt), where the screw 1104 is tightenable into bores of the arm 102 and the earpiece 104 to secure the arm 102 to the earpiece 104. For example, arm 102 may include an arm bore 1106 (i.e. hole) which is located near a proximal arm end 1108 (i.e. attachment point) of the arm 102, and the earpiece 104 may include an earpiece bore 1110, where the screw 1104 may pass through the arm bore 1106 and the earpiece bore 1110 and tighten or screw into the bores concurrently to attach the arm 102 to the earpiece 104. The earpiece bore 1110 may be located on the earpiece 104 such that when the earpiece 104 is worn, or supported, on the auricle 106, the earpiece bore 1110 is located posterior the auricle 106 (e.g. between the helix 110 and the head 112). The bores 1106 and 1110 may include internal threads for receiving an external thread of the screw 1104. The bores 1106 and 1110 may extend laterally from the arm 102 and earpiece 104, respectively. As such, the arm 102 may attach to the earpiece 104 such that the arm 102 is supported on the earpiece 104 and such that the proximal arm end 1108 of the arm 102 is located posterior the helix 110 or generally posterior the auricle 106 as shown in FIGS. 1-10. Once attached, a distal tip 1112 of the arm may extend past, around, and/or over a helix 110 of the auricle 106 for engaging and retaining the helix 110 and the auricle 106. It is to be understood that the arm 102 may also be configured to retain other portions of the ear such as lobular portions.

As shown in FIGS. 1-14, the arm 102 may be configured to curve upward and over the helix 110. For example, the arm 102 may have a lowercase "r" shape, or a hook shape to hook over the helix 110. The arm 102 may include two internal right angles to cause the arm 102 to curve downward, or position a distal tip 1112 downward back toward the helix 110.

It is to be understood that the arm 102 may be attached to the earpiece 104 via any appropriate method such as via snap-on or clip-on mechanisms and configurations. Further, the arm 102 may be selectively and removably attached to any appropriate location on the earpiece 104 for retaining the auricle 106. The arm 102 may be provided pre-attached to the earpiece 104. The arm may be fixedly or removably attached to the earpiece 104. The arm may be attached to a lateral surface of the earpiece 104, or a top or bottom surface of the earpiece 104. The arm 102 may be covered by a flexible plastic or rubber sheath for providing comfort to a user while the arm 102 engages the auricle 106. The arm 102 may be composed of a material that is malleable or pliable by a user, such as a malleable metal or plastic. The arm 102 being malleable allows a user to adapt the arm 102 to conform to their auricle 106 as needed to properly retain the auricle 106.

Figure 5:
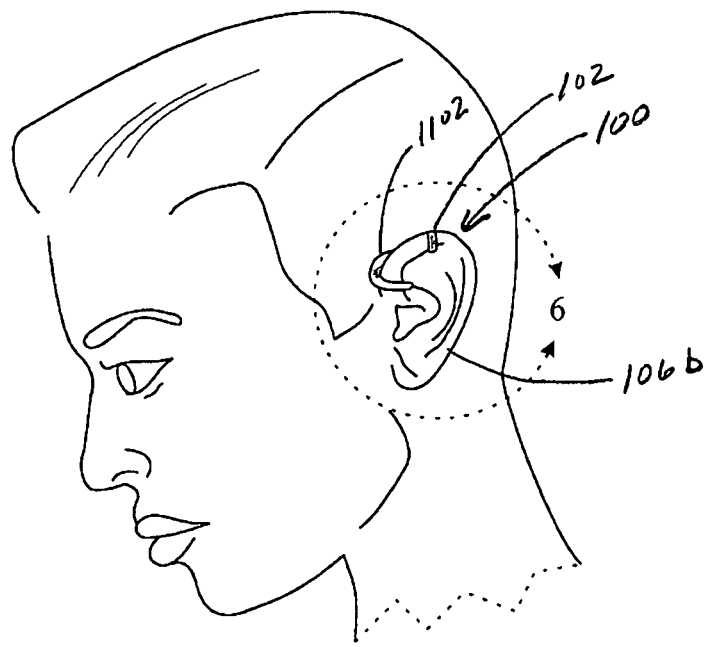
FIG. 5 shows a side view of an auricle retainer that is attached to an earpiece and being worn by a wearer.

As mentioned above, the earpiece 104 may be a curved earpiece 1102 as shown in FIGS. 5-12. The curved earpiece 1102 may include a curved engaging portion 1114 (e.g. a curved surface). The curved engaging portion 1114 is configured to engage the auricle 106 when worn as shown in FIG. 5. For example, the curved engaging portion 1114 may include a frontal curve portion 1116 having a smaller general radius of curvature than a radius of curvature of a posterior curve portion 1118. The frontal curve portion 1116 and the posterior curve portion 1118 may curve in a same general direction as shown in FIG. 11 (e.g. clockwise following from the posterior curve portion 1118 toward the frontal curve portion 1116), and may be continuous or connected with one another to form a curved space 1120 between internal surfaces of the curves. The curved space 1120 may receive auricle 106, and the curved earpiece 1102 may wrap around the auricle 106.

Figure 9:
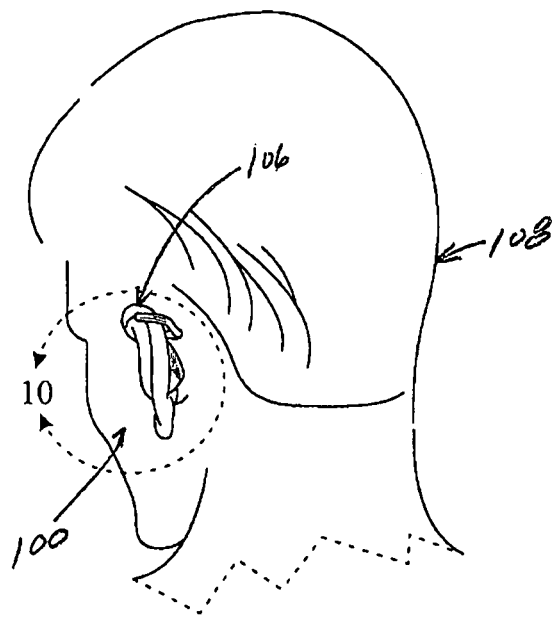
FIG. 9 shows a back view of the auricle retainer of FIG. 5 being worn by the wearer.
Figure 10:
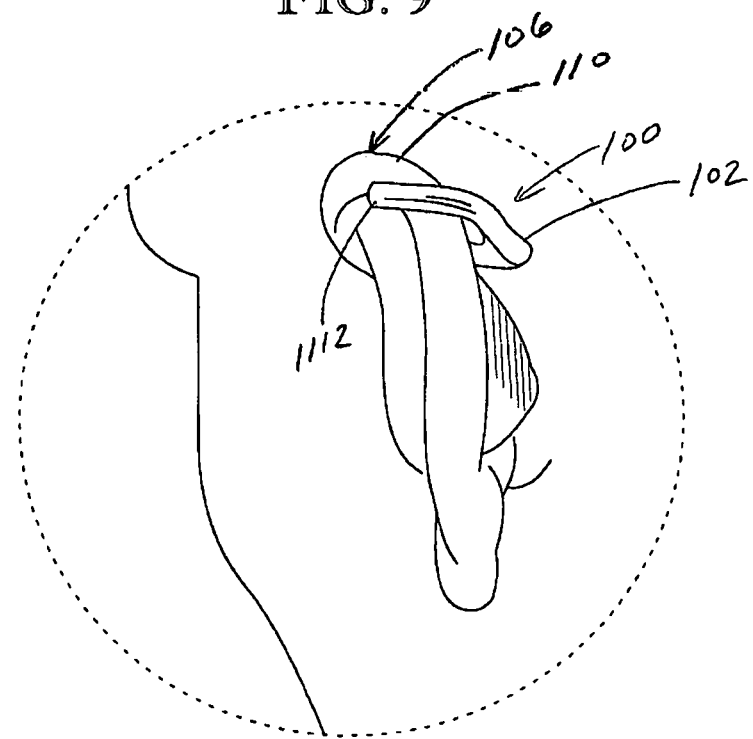
FIG. 10 shows a back close-up view of the auricle retainer of FIG. 5 being worn by the wearer.

For example, both the frontal curve portion 1116 and the posterior curve portion 1118 may curve (e.g. concavely downward) without an inflection point with respect to a longitudinal dimension of the curves. The frontal curve portion 1116 is configured to curve around a helix 110 when worn as shown in FIG. 5. The posterior curve portion 1118 is configured to curve around a posterior portion of the auricle 106 behind the auricle 106 as shown in FIG. 9. Therefore, in the curved earpiece 1102, the earpiece bore 1110 may be centrally located in the posterior curve portion 1118 for receiving the arm 102. However, the earpiece bore 1110 may be located in any appropriate location without departing from scope of this disclosure, such as closer to the frontal curve portion 1116.

The frontal curve portion 1116 and posterior curve portion 1118 may be laterally slanted with respect to one another, and with respect to a general longitudinal axis of the curved earpiece 1102. As another example, the frontal curve portion 1116 and posterior curve portion 1118 may generally curve in a same plane, where a longitudinal axis of the curved earpiece 1102 is generally co-linear with the plane.

Figure 1:
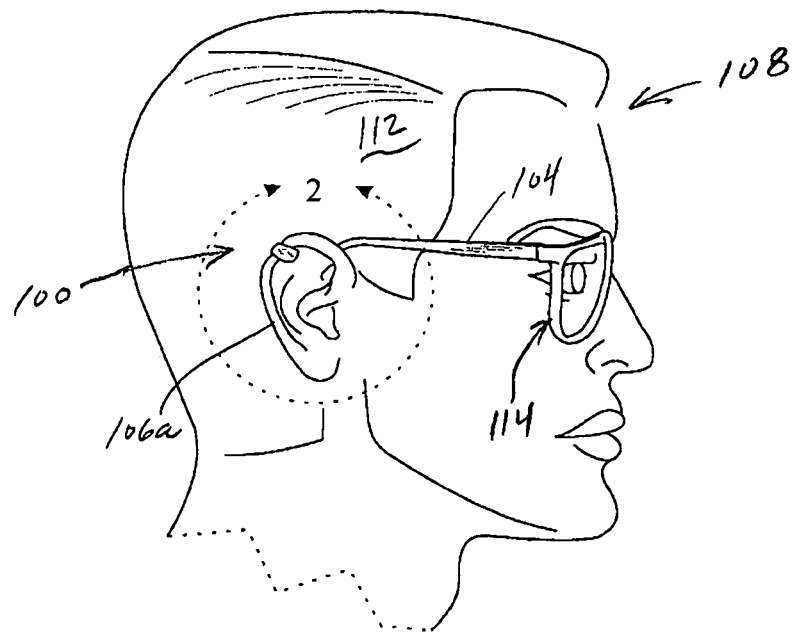
FIG. 1 shows a side view of an auricle retainer that is attached to eyewear and being worn by a wearer.

As also mentioned above, the earpiece 104 may be an eyewear earpiece 1302 as shown in FIGS. 1-4, 13 and 14. The eyewear earpiece 1302 may be or may include a temple tip portion 1304 of a set of eyeglasses 114 as shown in FIG. 1. As shown in FIG. 13, the arm 102 may be attachable to an earpiece bore 1110 which is located between a temple tip curve 1306 and a longitudinal distal end 1308 of the temple tip portion 1304. It is to be understood that the eyewear earpiece 1302 may be considered a general temple portion of a set of eyeglasses which is configured to fold with respect to lenses 116 of the eyeglasses 114.

It is to be understood that although the figures show examples of a curved earpiece and an eyewear earpiece, any appropriate structure may be considered an earpiece for attaching the arm 102, such as head bands or hats or other headwear. It is to be understood that both temple portions of the eyeglasses 114 may include the arm 102 for retaining both auricles 106 of the wearer 108. Further, using the curved earpiece 1102, the wearer 108 may wear one auricle retainer 100 on each ear for retaining both ears. It is also to be understood that the auricle retainer 100 may be used to push out the auricle 106 instead of pull in the auricle 106.

A method of use may include placing the earpiece 104 on the auricle 106, and bending, rotating, and/or manipulating the arm 102 such that the arm 102 clamps, holds, and/or grabs the auricle 106 or the helix 110 and retains the auricle 106 in a desired position. The arm 102 may rotate about an attachment point (e.g. earpiece bore 1110) for being appropriately adjusted for engaging and retaining the auricle 106.

As such, the auricle 106 may be retained to a symmetrical position or a frontally aerodynamic position as desired by a user (e.g. in sports applications to reduce drag). FIGS. 1-10 show the auricle retainer 100 in use where the arm 102 is retaining auricle 106 by extending from a posterior region of the auricle 106 over the helix 110. As shown in FIGS. 11-14, the arm 102 may be attached, or attachable such that the arm 102 is located between the earpiece 104 and the auricle 106. However, the scope of this disclosure is not limited to such arrangement of the arm, and the arm may be disposed between the earpiece 104 and the head 112 of the wearer. Further, it is to be understood that the earpiece 104 may be curved to ergonomically match the auricle 106 or the head 112 of the wearer.

The present invention is also an eyeglass frame or eyeglasses 114 having a skull temple or earpiece 104 having a bend or temple tip curve 1306, a proximal or attachment end 1310 to the eyeglasses 114, and a free end or distal end of the temple tip 1308, further having a hook or arm 102 disposed on the earpiece 104 between the distal end of the temple tip 1308 and the temple tip curve 1306, the arm 102 extending radially outward from the earpiece 104, the arm 102 for hooking onto a helix 110 of a wearer's ear or auricle 106 and pulling the helix 110 toward the earpiece 104 and wearer's head 112.

Figure 2:
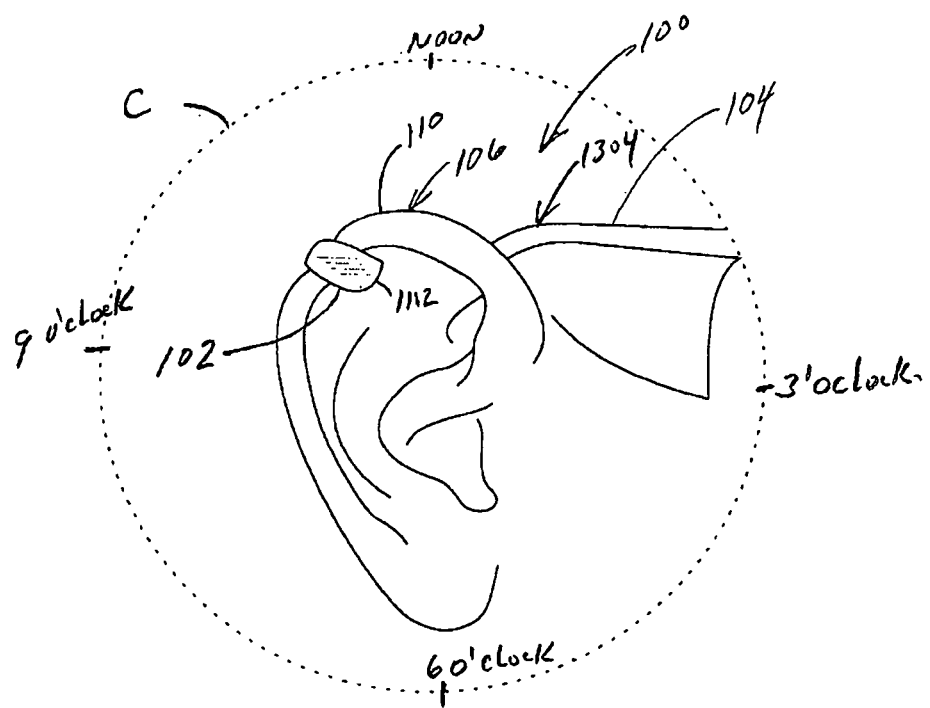
FIG. 2 shows a side close-up view of the auricle retainer of FIG. 1 being worn by the wearer.
Figure 3:
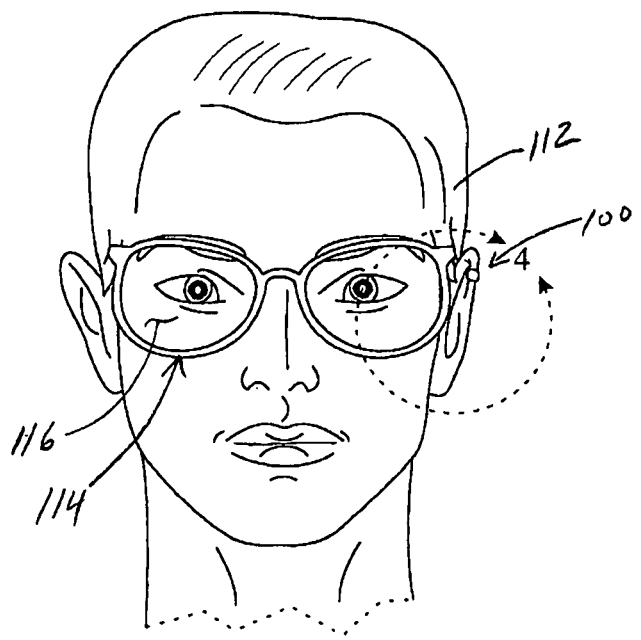
FIG. 3 shows a front view of the auricle retainer of FIG. 1 being worn by the wearer.
Figure 4:
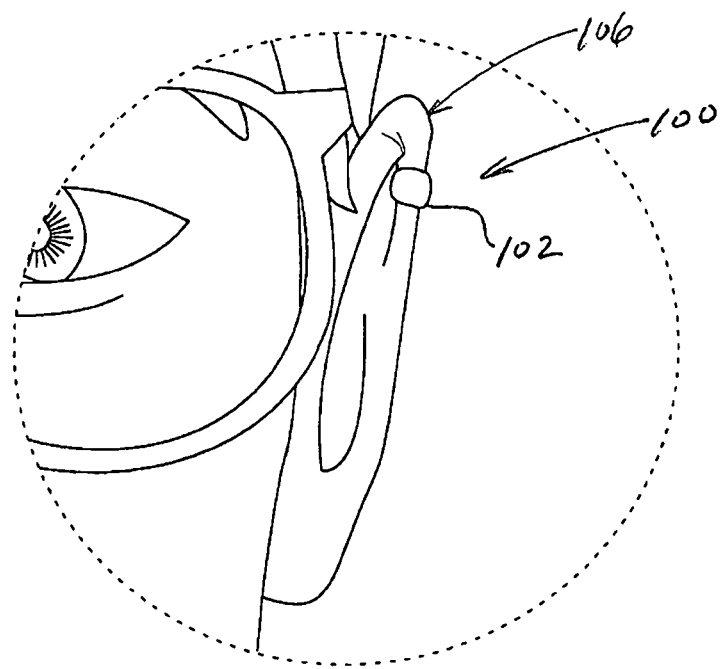
FIG. 4 shows a front close-up view of the auricle retainer of FIG. 1 being worn by the wearer.

Further, referring to FIG. 2, to describe positions of the arm 102 relative to the auricle 106 for the right auricle 106a of the wearer 108, the 9 o'clock position and the noon positions are shown with the 3 o'clock and 6 o'clock positions, as if the circle C was a 12 hour clock. The arm 102 engages the helix 110 between the 9 o'clock position and the noon position on a wearer's right auricle 106a. Specifically, in FIG. 2, the arm 102 engages the helix 110 of the right auricle 106a at the approximate 10 o'clock position.

Figure 6:
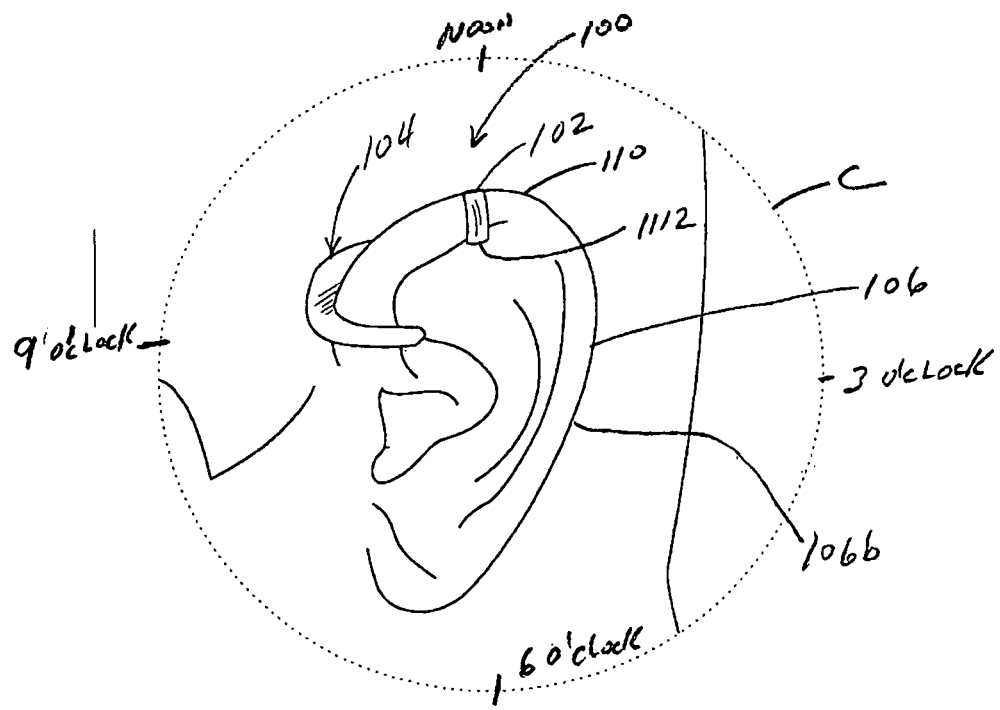
FIG. 6 shows a side close-up view of the auricle retainer of FIG. 5 being worn by the wearer.
Figure 7:
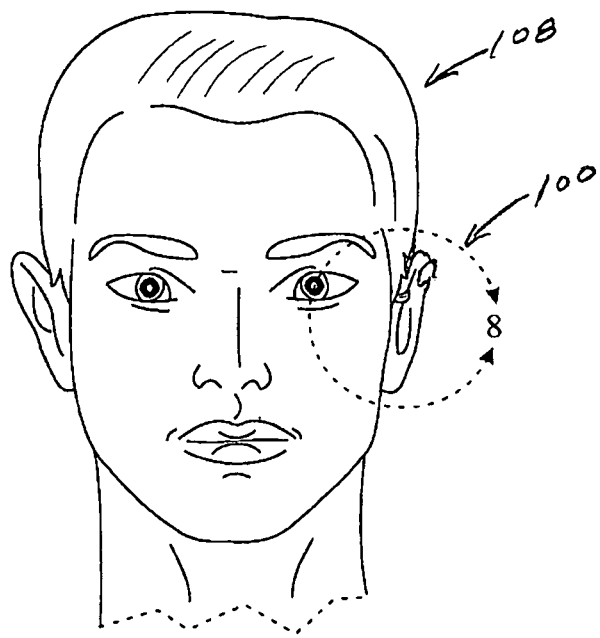
FIG. 7 shows a front view of the auricle retainer of FIG. 5 being worn by the wearer.
Figure 8:
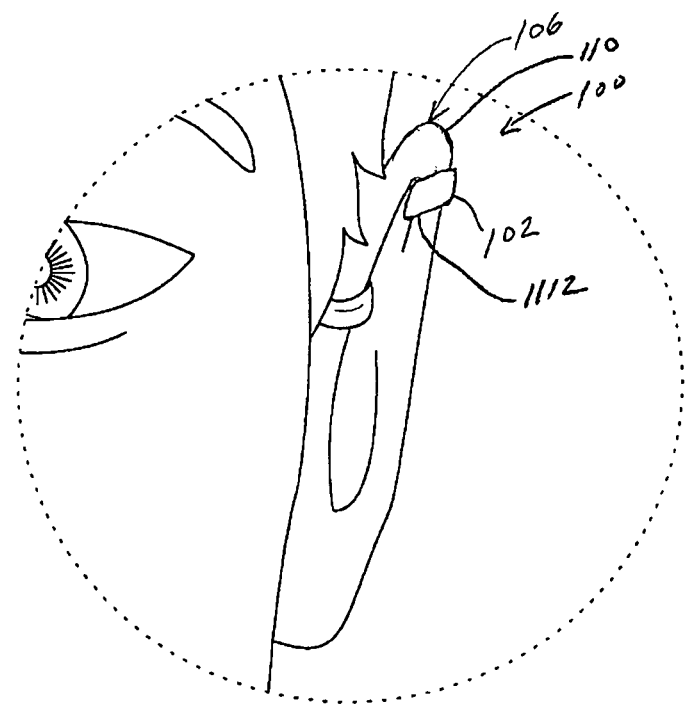
FIG. 8 shows a front close-up view of the auricle retainer of FIG. 5 being worn by the wearer.

Further, referring to FIG. 6, to describe positions of the arm 102 relative to the auricle 106 for the left auricle 106b of the wearer 108, the noon position and the 3 o'clock positions are shown with the 9 o'clock and 6 o'clock positions, as if the circle C was a 12 hour clock. The arm 102 engages the helix 110 between the noon position and the 3 o'clock position on a wearer's left auricle 106b. Specifically, in FIG. 6, the arm 102 engages the helix 110 of the left auricle 106b at the approximate noon position. Thus in comparison between FIG. 2 and FIG. 6, the arm 102 can be located at various positions along the helix 110.

The present invention is also an ear flatting device or auricle retainer 100 having an earpiece hook or earpiece 104 for engaging a wearer's ear or auricle 106 and holding the auricle retainer 100 on the ear or auricle 106, the earpiece 104 having a shank 1114a, the shank 1114a engaging around a wearer's 108 posterior provenance of the superior concha (a part of the auricle 106) and pointing in a rear direction of the wearer's head 112, and a hold down hook or arm 102 for engaging over a wearer's helix 110 and pulling the helix 110 towards the wearer's head 112, the arm 102 having a hold down hook shank 1312 with a shank end or proximal arm end 1108, the proximal arm end 1108 being affixed at the shank 1114a of the earpiece 104. The arm 102 having a bend 1316 with a front length 1318, the front length 1318 being disposed between 12 o'clock and 3 o'clock relating to a left auricle 106b of the wearer 108 when the auricle retainer 100 is disposed on the left auricle 106b as a clock is described in FIG. 6, and the front length 1318 being disposed between 12 o'clock and 9 o'clock relating to a right auricle 106b of the wearer 108 when the auricle retainer 100 is disposed on the right auricle 106a as a clock is described and shown in FIG. 2.

Further, the arm 102 has a bend 1316 leading to a distal tip 1112 and the earpiece 104 has a bend or curve portion 1116 leading to a distal tip 1116a, both bend 1316 and curve portion 1116 being in a same clock direction counter clockwise for the left ear or auricle 106b and clockwise for the right ear or auricle 106a as shown in FIGS. 6 and 2 respectively.

Further the arm 102 is mounted to be pivotally adjusted on the earpiece 104.

In conclusion, disclosed is an auricle retainer that is configured to conveniently retain an auricle of a wearer. The auricle retainer may include an earpiece and an arm connected to the earpiece. The arm may be configured to engage a helix of the auricle for retaining the auricle.

I claim:

1. Eyeglass frames comprising:
   a skull temple having a bend, an attachment end, a free end, and a temple tip portion between said bend and said free end, said bend turning said temple tip portion downward for disposition behind a wearer's ear in a worn position of the eyeglass frames;
   a hook disposed on said skull temple attached at said temple tip portion, said hook extending radially outward from said temple, said hook for hooking onto a helix of a wearer's ear and pulling the helix toward said temple and wearer's head.

2. The eyeglass frames at claim 1 wherein said hook is configured to engage the helix between 9 o'clock and noon on a wearer's right ear.

3. The eyeglass frame at claim 1, wherein said hook is configured to engage the helix between noon and 3 o'clock on the wearer's left ear.

* * * * *